United States Patent
Cao

(10) Patent No.: US 6,955,690 B1
(45) Date of Patent: Oct. 18, 2005

(54) MAMMARY PROSTHESIS MADE OF POLYACRYLAMIDE HYDROGEL

(76) Inventor: Mengjun Cao, No. 1004, Huangbei Road, Luohu District, Shenzhen, Guangdong (CN) 518003

( * ) Notice: Subject to any disclaimer, the term of this patent is extended or adjusted under 35 U.S.C. 154(b) by 105 days.

(21) Appl. No.: 10/070,289

(22) PCT Filed: Aug. 30, 2000

(86) PCT No.: PCT/CN00/00254

§ 371 (c)(1),
(2), (4) Date: Jul. 15, 2002

(87) PCT Pub. No.: WO01/17573

PCT Pub. Date: Mar. 15, 2001

(30) Foreign Application Priority Data

Sep. 7, 1999 (CN) ............................... 99242660 U

(51) Int. Cl.⁷ ............................................. A61F 2/02
(52) U.S. Cl. .............................. 623/7; 623/8; 623/11.11
(58) Field of Search ............................ 623/11.11, 7–8

(56) References Cited

U.S. PATENT DOCUMENTS

| | | | |
|---|---|---|---|
| 4,657,553 A | * | 4/1987 | Taylor ............................ 623/8 |
| 5,376,117 A | * | 12/1994 | Pinchuk et al. ................. 623/8 |
| 5,658,329 A | | 8/1997 | Purkait |
| 5,941,909 A | * | 8/1999 | Purkait .................... 623/23.72 |
| 6,051,648 A | * | 4/2000 | Rhee et al. ................. 525/54.1 |
| 6,692,528 B2 | * | 2/2004 | Ward et al. .............. 623/17.12 |

FOREIGN PATENT DOCUMENTS

EP  0 784 987 A2  *  1/1997  ................... 623/7

* cited by examiner

*Primary Examiner*—Suzette J-J Gherbi
(74) *Attorney, Agent, or Firm*—Merchant and Gould P.C.

(57) ABSTRACT

The present invention relates to a mammary prosthesis made of polyacrylamide hydrogel. Said prosthesis include a shell which is made of medical high polymer elastic material, such as silicone, and said shell have a round curved surface. The shell is filled with polyacrylamide hydrogel, or with hydrogel powder, and the weight of the filled powder is matched with the volume of the circular shell, that is to say, each 100 ml volumes of the shell could be filled with about 2.5–5 g hydrogel powder.

14 Claims, 2 Drawing Sheets

MAMMARY PROSTHESIS MADE OF POLYACRYLAMIDE HYDROGEL

FIELD OF THE INVENTION

The present invention relates to a medical plastic cosmetic surgery material. More specifically, it relates to a kind of mammary prosthesis that is used in plastic and cosmetic surgery.

BACKGROUND OF THE INVENTION

A mammary prosthesis made of liquid silicon or silicon gel had been applied to be implanted into the breasts in traditional plastic surgery for breasts. Although they felt good and enhanced breast beauty, there existed the problem of silicon leakage or spontaneous implant rapture. And the toxic silicon could induce breast granuloma and affect the immunological functions of the body, and could be even carcinogenic. In order to solve these problems, saline, vegetable oil and protolysate are filled into the mammary prosthesis. Although this can partially solve the problem of toxicity and other complications, they do not feel as natural as liquid silicon implants.

OBJECTS OF THE INVENTION

The object of the present invention is to provide a new type of mammary prosthesis which can overcome the drawbacks mentioned above. The mammary prosthesis feels good and guarantees safety, whether it is ruptured or not.

SUMMARY OF THE INVENTION

The object of the present invention can be implemented by constructing mammary prosthesis made of polyacrylamide hydrogel, which comprising a shell 2 that is made of medical high polymer elastic material; said shell 2 is filled with polyacrylamide hydrogel 4.

In the above mammary prosthesis, said medical high polymer elastic material is silicone.

In the above mammary prosthesis, said polyacrylamide hydrogel 4 is made by adding 2.5–7 g polyacrylamide dry powder into every 100 ml water.

In the above mammary prosthesis, the weight percentage of said polyacrylamide hydrogel 4 is: 2.5–8% acylamide, 0.001–3.0% cross-linking agent, 0.001–4.00% catalyst, 0.001–2.00% accelerator, 0.001–2.00% facilitator and the other is sterile secondary distilled water.

In the above mammary prosthesis, said cross-linking agent is N,N'-methylenebisacrylamide and its homologous compound, or N,N'-diallyltartratdiamide; and said catalyst is ammonium persulfate or kalium persulfate; and said accelerator can be sodium bisulphate or sodium metasulphite; and said facilitators include triethanolamide, triethlamine or their N,N'ethylenediamine substances which contains substituting groups.

In the above mammary prosthesis, said shell 2 has a round curved surface.

The objects of the present invention also can be achieved by constructing a mammary prosthesis made of polyacrylamide hydrogel, comprising a shell 2 that is made of medical high polymer elastic material; said shell 2 is filled with dry powder 3 of polyacrylamide hydrogel whose weight is matched with the value of the circular shell, that is to say, each 100 ml volumes of the shell could be filled with 2.5–7 grams of said dry powder 3. Wherein said shell 2 has a non-return valve 1.

In the above mammary prosthesis, each 100 ml volumes of the shell 2 could be filled with 4 grams of said dry powder 3.

In the above mammary prosthesis, said medical high polymer elastic material is silicone.

In the above mammary prosthesis, said polyacrylamide hydrogel dry powder in weight comprises 2.5–8 units of acrylamide, 0.001–3.0 units of cross-linking agent, 0.001–4 units of catalyst, 0.001–2.00 units of accelerator, 0.001–2.00 units of facilitator.

In the above mammary prosthesis, said cross-linking agent is N,N'-methylenebisacrylamide and its homologous compound, or N,N'-diallyltartratdiamide; and said catalyst is ammonium persulfate or kalium persulfate; and said accelerator can be sodium bisulphate or sodium metasulphite; and said facilitators include triethanolamide, triethlamine or their ethylenediamine substances which contains substituting groups.

In the above mammary prosthesis, said shell 2 has a round curved surface.

In the above mammary prosthesis, said non-return valve 1 is located in the center of one face of said round shell 2.

The mammary prosthesis made of polyacrylamide hydrogel of the present invention has the advantages of feeling true, convenience for use, non-toxicity after long-term, safety and without sequela, etc.

The present invention will be understood by reference to description taken in conjunction with accompanying drawing in which:

BRIEF DECRIPTION OF THE DRAWINGS

DESCRIPTION OF THE PREFERRED EMBODIMENTS

Figure 1:
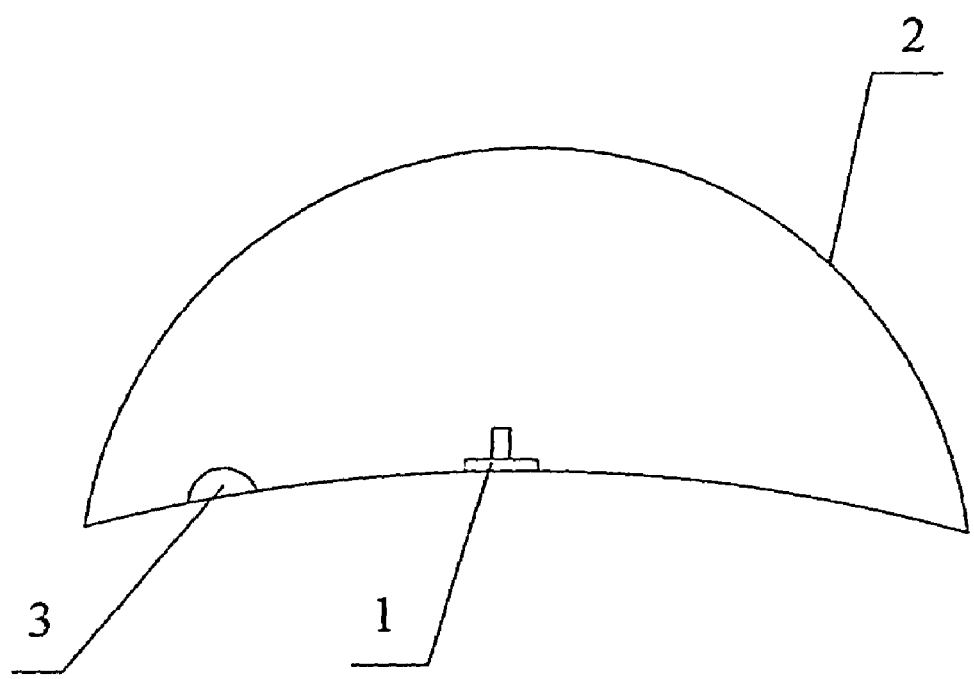
FIG. 1 is a side view of the mammary prosthesis made of polyacrylamide hydrogel in an embodiment of the present invention.

As shown in FIG. 1, the mammary prosthesis made of polyacrylamide hydrogel of the present invention has an outer shell 2 which has a round curved surface. Said shell 2 is made of flexible silicon, and a non-return valve 1 is located in the center of one face of said shell 2. Said valve 1 is used for injecting saline into the prosthesis after it is implanted into the human body. Beforehand said shell 2 is filled with dry powder 3 of polyacrylamide hydrogel whose weight is matched with the volume of said circular shell 2; for example each 100 ml volumes of the shell could be filled with 2.5–7 g (4 g preferably) of said dry powder 3.

Figure 2:
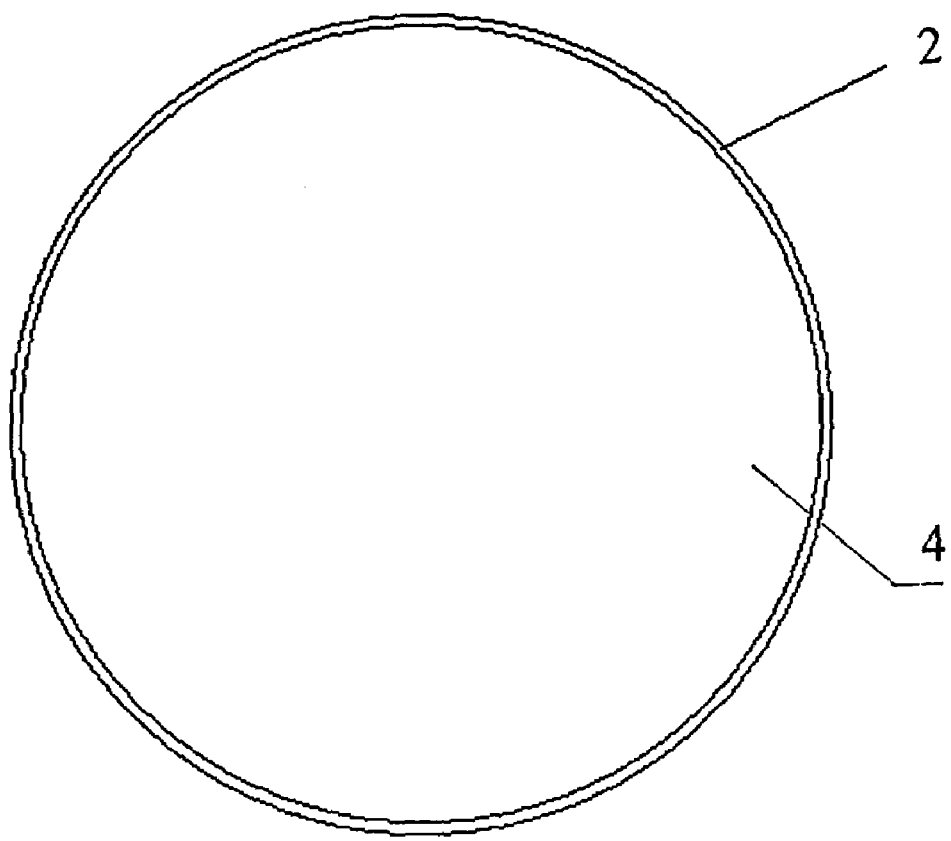
FIG. 2 is a front view of the mammary prosthesis made of polyacrylamide hydrogel in another embodiment of the present invention.

As shown in FIG. 2, in another embodiment of the present invention, the prepared polyacrylamide hydrogel 4 is filled in the shell beforehand. The shell 2 should have a round curved surface. And the shell needs no non-return valve.

In the above embodiments, the polyacrylamide hydrogel is prepared in the following way: take cross-linked acrylamide as the base, and diffuse proper amount of acrylamide, cross-linking agent, catalyst, accelerator and facilitator into sterile secondary distilled water to polymerize, then the gel resulted from this kind of polymerization is washed, soaked and extracted, and finally medical gel of different cross-linking degrees and densities is prepared.

What is claimed is:

1. A mammary prosthesis made of polyacrylamide hydrogel, comprising shell which is made of silicon, and polyacrylamide hydrogel filled in said shell, said polyacrylamide hydrogel being prepared by adding 2.5–7 grams of polyacrylamide dry powder into every 100 ml water, said polyacrylamide hydrogel dry powder comprising a weight percentage of 2.5–8% acylamide, 0.001–3.0% cross-linking agent, 0.001–4.00% catalyst, 0.001–2.00% accelerator, 0.001–2.00% facilitator are added into distilled water to be 100% to be polymerized, then be washed, soaked, centrifugal dehydrated and dried.

2. A mammary prosthesis as claimed in claim 1 wherein said cross-linking agent is N, N'-methylenebisacrylamide and its homologous compound, or N, N'-diallyltartratdiamide.

3. A mammary prosthesis as claimed in claim 1 wherein said shell has a round curved surface.

4. A mammary prosthesis as claimed in claim 2 wherein said catalyst is ammonium persulfate or kalium persulfate.

5. A mammary prosthesis as claimed in claim 4 wherein said accelerator is sodium bisulphate or sodium metasulphite.

6. A mammary prosthesis as claimed in claim 5 wherein said facilitators comprise triethanolamide, triethlamine or their N,N'ethylenediamine substances which contains substituting groups.

7. A mammary prosthesis made of polyacrylamide hydrogel wherein it comprises a shell that is made of silicon and has a non-return valve, and said shell comprises dry powder of polyacrylamide hydrogel whose weight is proportional to the volume (ml) of said shell; wherein 2.5–7 grams of said dry powder of polyacrylamide hydrogel is added to every 100 ml volume of said shell, and said dry powder comprises a weight percentage of 2.5–8% acylamide, 0.001–3.0% cross-linking agent, 0.001–4.00% catalyst, 0.001–2.00% accelerator, 0.001–2.00% facilitator are added into distilled water to be 100% polymerized, then washed, soaked, centrifugal dehydrated and dried.

8. A mammary prosthesis as claimed in claim 7 wherein 4 grams of said dry powder is added to every 100 ml volume of said shell.

9. A mammary prosthesis as claimed in claim 8 wherein said cross-linking agent is N,N'-methylenebisacrylamide and its homologous compound, or N,N'-diallyltartratdiamide.

10. A mammary prosthesis as claimed in claim 9 wherein said catalyst is ammonium persulfate or kalium persulfate.

11. A mammary prosthesis as claimed in claim 10 wherein said accelerator is sodium bisulphate or sodium metasulphite.

12. A mammary prosthesis as claimed in claim 11 wherein said facilitators comprise triethanolamide, triethlamine or their N,N'ethylenediamine substances which contains substituting groups.

13. A mammary prosthesis as claimed in claim 7 wherein said shell has a round curved surface.

14. A mammary prosthesis as claimed in claim 7 wherein said non-return valve is located in the center of one face of said shell.

* * * * *